United States Patent
Yamashita et al.

(10) Patent No.: US 10,092,514 B2
(45) Date of Patent: *Oct. 9, 2018

(54) EYE DROP WITH DIFLUPREDNATE FOR MACULAR EDEMA TREATMENT

(71) Applicant: YAMAGATA UNIVERSITY, Yamagata (JP)

(72) Inventors: Hidetoshi Yamashita, Yamagata (JP); Teiko Yamamoto, Tokyo (JP); Sakiko Goto, Yamagata (JP); Sachi Abe, Yamagata (JP); Eriko Kirii, Yamagata (JP); Atsushi Okumura, Osaka (JP)

(73) Assignee: YAMAGATA UNIVERSITY, Yamagata (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,744

(22) Filed: Jan. 10, 2018

(65) Prior Publication Data

US 2018/0133153 A1    May 17, 2018

Related U.S. Application Data

(63) Continuation of application No. 14/661,295, filed on Mar. 18, 2015, now Pat. No. 9,949,926, which is a continuation of application No. 13/122,467, filed as application No. PCT/JP2010/062289 on Jul. 14, 2010, now abandoned.

(30) Foreign Application Priority Data

Jul. 14, 2009  (JP) .................................. 2009-165924

(51) Int. Cl.
| | |
|---|---|
| *A61K 31/573* | (2006.01) |
| *A61K 9/107* | (2006.01) |
| *A61K 9/00* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61K 47/22* | (2006.01) |
| *A61K 47/46* | (2006.01) |

(52) U.S. Cl.
CPC ............ *A61K 9/107* (2013.01); *A61K 9/0048* (2013.01); *A61K 31/573* (2013.01); *A61K 47/02* (2013.01); *A61K 47/10* (2013.01); *A61K 47/12* (2013.01); *A61K 47/183* (2013.01); *A61K 47/22* (2013.01); *A61K 47/46* (2013.01)

(58) Field of Classification Search
CPC .................................................. A61K 31/573
See application file for complete search history.

(56) References Cited

U.S. PATENT DOCUMENTS

| | | |
|---|---|---|
| 6,114,319 A | 9/2000 | Kimura |
| 2005/0048099 A1 | 3/2005 | Shiah et al. |
| 2006/0154910 A1 | 7/2006 | Bingaman et al. |
| 2009/0105245 A1 | 4/2009 | Bingaman |

FOREIGN PATENT DOCUMENTS

| | | |
|---|---|---|
| EP | 0 878 197 | 11/1998 |
| WO | 2005/099717 | 10/2005 |
| WO | 2006/082588 | 8/2006 |
| WO | 2007/025275 | 3/2007 |

OTHER PUBLICATIONS

International Search Report dated Jul. 14, 2009 in International (PCT) Application No. PCT/JP2010/062289 along with the Written Opinion.
M. S. Korenfeld et al., "Difluprednate Ophthalmic Emulsion 0.05% for Postoperative Inflammation and Pain", Journal of Cataract Refractive Surgery, vol. 35, No. 1, pp. 26-34, 2009.
A. Martidis et al., "Intravitreal Triamcinolone for Refractory Diabetic Macular Edema", Ophthalmology, vol. 109, No. 5, pp. 920-927, 2002.
S. Nakano et al., "Steroid Eye Drop Treatment (Difluprednate Ophthalmic Emulsion) is Effective in Reducing Refractory Diabetic Macular Edema", Graefe's Archive for Clinical and Experimental Ophthalmology, vol. 284, No. 6, pp. 805-810, 2010.
The 43rd Annual Congress of Japanese Retina and Vitreous Society, 016-5, Dec. 2004 with English translation.
Chinese Office Action (with English translation) dated Sep. 28, 2012 in corresponding Chinese Patent Application No. 201080002750.2.
Third Party Observation under section 34.1 of the Patent Act of Canada submitted by Dr. Archana Sharma dated May 3, 2014 in Canadian Patent Application No. 2,738,151.
Acknowledgement of Third Party Observation from Canadian Intellectual Property Office dated Jun. 4, 2014 in Canadian Patent Application No. 2,738,151.
Russian Decision on Grant of Patent issued in Russian Patent Application No. 2011125640/15(037872).
Tajika et al., "Ocular Distribution and Metabolism after Instillation of Difluprednate Ophthalmic Emulsion in Rabbits", ARVO RESEARCH presented at the 2007 Annual Meeting of the Association of Research in Vision and Ophthalmology, May 6, 2007, 1 page.
Final Written Decision for Case IPR2015-01205 regarding U.S. Pat. No. 6,114,319 dated Nov. 22, 2016, pp. 1-28.

*Primary Examiner* — Zohreh A Fay
(74) *Attorney, Agent, or Firm* — Wenderoth, Lind & Ponack, L.L.P.

(57) ABSTRACT

The present invention aims to provide an eye drop for treating macular edema. The present invention provides an eye drop for treating macular edema, which contains difluprednate as an active ingredient. The eye drop can afford effects such as improvement of visual acuity and decreased foveal retinal thickness in macular edema.

28 Claims, No Drawings

EYE DROP WITH DIFLUPREDNATE FOR MACULAR EDEMA TREATMENT

TECHNICAL FIELD OF THE INVENTION

The present invention relates to an eye drop containing difluprednate as an active ingredient for treating macular edema.

BACKGROUND OF THE INVENTION

Macular edema is swelling of retinal macula, and the edema occurs due to a liquid diapedesis from the retinal blood vessels. The blood leaks from weak blood vessel walls and enters into extremely small regions of retinal macula rich in retina cone which is a nerve terminal that detects color and the vision during the day relies on. Next, images become blurred in the center of the central field or right beside the center. The visual acuity decreases progressively for months. Diabetic retinopathy, retinal blood vessel obstruction, ocular inflammation and age-related macular degeneration are all associated with the macular edema. Retinal macula is sometimes damaged by maculatumentia after removal of crystalline lens for the treatment of cataract.

As the conventional therapy of macular edema, photocoagulation by laser irradiation, vitreous surgery and systemic administration, intravitreal administration and sub-Tenon administration of steroid and the like have been performed. The photocoagulation by laser irradiation closes the blood vessel permitting liquid diapedesis, and decreases swelling of macula. However, attention should be paid in laser irradiation to avoid extremely vulnerable fovea. If the fovea should be injured by this surgery, the central visual field may be damaged. Moreover, plural laser surgeries are often required to eliminate swelling. While vitreous surgery is applied to a case for which a laser surgery is ineffective, it is associated with high tissue-invasive potential, sometimes causing problems of post-surgery complications. In addition, the administration of steroid is reported to be useful. While systemic administration of steroid is possible for the treatment of ocular diseases, in general, it often causes side effects which are too severe for ophthalmologic uses. Therefore, intravitreal administration and sub-Tenon administration, which are topical administrations, have also been studied. Although intravitreal administration can solve some problems associated with systemic administration, intravitreal administration of existing ophthalmic compositions can cause ocular hypertension, steroid glaucoma and posterior subcapsular cataract when steroid is administered. Also, intravitreal administration of steroid sometimes causes post-surgery complications. sub-Tenon administration is often used in clinical practice to decrease the tissue-invasive potential of intravitreal administration and burden on patients. While administration of steroid decreases the tissue-invasive potential as compared to vitreous surgery, it is still associated with the problems of post-surgery complications.

Administration by instillation is an administration method with high merit since it has low tissue-invasive potential. Examples of the treatment of ophthalmic diseases by instillation of steroid include use of a 0.1% betamethasone ophthalmic solution for anti-inflammatory diseases (blepharitis, conjunctivitis, keratitis, scleritis, episcleritis, anterior ocular segmentuveitis, postoperative inflammation) in the external eye and the anterior ocular segment. Moreover, WO 2007/025275 describes the possibility of application of instillation and the like of various steroids and corticosteroid antagonists to the treatment of various ophthalmic diseases such as macular degeneration, glaucoma, macular edema, age-related macular degeneration, retina angiogenesis, diabetic retinopathy, iritis, posterior eye segmentuveitis and the like, while decreasing the side effects of steroid. However, only few cases of effectiveness of instillation for macular edema of the retina in clinical practice have been reported, and there is only one report of volume reduction of retinal macular edema by administration of 0.1% betamethasone ophthalmic solution for 2 weeks to one month, 6 times per day (The 43rd Annual Congress of Japanese Retina and Vitreous Society O16-5, 2004). Thus, the treatment of macular edema by eye drop has not been performed.

SUMMARY OF THE INVENTION

Problems to be Solved by the Invention

The present invention aims to provide an eye drop for the treatment of macular edema.

Means of Solving the Problems

The present inventors have conducted intensive studies in an attempt to solve the aforementioned problems and found that administration of an eye drop containing difluprednate as an active ingredient improves the symptoms of decreased visual acuity, increased foveal retinal thickness and the like due to macular edema, which resulted in the completion of the present invention.

Accordingly, the present invention provides the following.

(1) An eye drop for treating macular edema, comprising difluprednate as an active ingredient.
(2) The eye drop of (1), wherein the macular edema is refractory macular edema.
(3) The eye drop of (1) or (2), which is an emulsion eye drop.
(4) The eye drop of any of (1) to (3), wherein the concentration of difluprednate is 0.005-0.1% (w/v).
(5) The eye drop of any of (1) to (4), comprising 0.005-0.1% (w/v) of difluprednate, and castor oil, polysorbate 80, concentrated glycerin, sodium acetate, boric acid, sodium edetate and sorbic acid.
(6) The eye drop of any of (1) to (5), wherein the concentration of difluprednate is 0.005-0.1% (w/v), a dosing period is at least 1 week, an administration frequency is 4 times per day, and a dose is 30-50 μL per administration.
(7) The eye drop of any of (1) to (5), wherein the concentration of difluprednate is 0.005-0.1% (w/v), a dosing period is 1-4 weeks, an administration frequency is. 4 times per day, and a dose is 30-50 μL per administration.
(8) The eye drop of any of (1) to (5), wherein the concentration of difluprednate is 0.005-0.1% (w/v), an administration frequency is 4 times per day for 4 weeks from the start of the administration and twice per day after 4 weeks, and a dose is 30-50 μL per administration.
(9) The eye drop of any of (1) to (5), wherein the concentration of difluprednate is 0.005-0.1% (w/v), a dosing period is not longer than 12 weeks, an administration frequency is 4 times per day for 4 weeks from the start of the administration and twice per day after 4 weeks, and a dose is 30-50 μL per administration.
(10) The eye drop of any of (1) to (5), wherein the concentration of difluprednate is 0.005-0.1% (w/v), a dosing period is at least 12 weeks, an administration frequency is 4 times per day for 4 weeks from the start of the administration and twice per day after 4 weeks, and a dose is 30-50 μL per administration.

(11) A method of treating macular edema in a mammal, comprising instilling an eye drop containing an effective amount of difluprednate to the mammal.

(12) The method of (11), wherein the macular edema is refractory macular edema.

(13) The method of (11) or (12), wherein the eye drop is an emulsion eye drop.

(14) The method of any of (11) to (13), wherein the concentration of difluprednate in the eye drop is 0.005-0.1% (w/v).

(15) The method of any of (11) to (14), wherein the eye drop comprises 0.005-0.1% (w/v) of difluprednate, and castor oil, polysorbate 80, concentrated glycerin, sodium acetate, boric acid, sodium edetate and sorbic acid.

(16) The method of any of (11) to (15), wherein the concentration of difluprednate in the eye drop is 0.005-0.1% (w/v), and the eye drop is administered for at least 1 week, 4 times per day, in a dose of 30-50 μL per administration.

(17) The method of any of (11) to (15), wherein the concentration of difluprednate in the eye drop is 0.005-0.1% (w/v), and the eye drop is administered for 1-4 weeks, 4 times per day, in a dose of 30-50 μL per administration.

(18) The method of any of (11) to (15), wherein the concentration of difluprednate in the eye drop is 0.005-0.1% (w/v), and the eye drop is administered 4 times per day for 4 weeks from the start of the administration and twice per day after 4 weeks, in a dose of 30-50 μL per administration.

(19) The method of any of (11) to (15), wherein the concentration of difluprednate in the eye drop is 0.005-0.1% (w/v), and the eye drop is administered for not longer than 12 weeks, 4 times per day for 4 weeks from the start of the administration and twice per day after 4 weeks, in a dose of 30-50 μL per administration.

(20) The method of any of (11) to (15), wherein the concentration of difluprednate in the eye drop is 0.005-0.1% (w/v), and the eye drop is administered for at least 12 weeks, 4 times per day for 4 weeks from the start of the administration and twice per day after 4 weeks, in a dose of 30-50 μL per administration.

(21) An eye drop containing difluprednate for use in the treatment of macular edema.

(22) The eye drop of (21), wherein the macular edema is refractory macular edema.

(23) The eye drop of (21) or (22), which is an emulsion eye drop.

(24) The eye drop of any of (21) to (23), wherein the concentration of difluprednate is 0.005-0.1% (w/v).

(25) The eye drop of any of (21) to (24), comprising 0.005-0.1% (w/v) of difluprednate, and castor oil, polysorbate 80, concentrated glycerin, sodium acetate, boric acid, sodium edetate and sorbic acid.

(26) The eye drop of any of (21) to (25), wherein the concentration of difluprednate is 0.005-0.1% (w/v), and the eye drop is administered for at least 1 week, 4 times per day, in a dose of 30-50 μL per administration.

(27) The eye drop of any of (21) to (25), wherein the concentration of difluprednate is 0.005-0.1% (w/v), and the eye drop is administered for 1-4 weeks, 4 times per day, in a dose of 30-50 μL per administration.

(28) The eye drop of any of (21) to (25), wherein the concentration of difluprednate is 0.005-0.1% (w/v), and the eye drop is administered 4 times per day for 4 weeks from the start of the administration and twice per day after 4 weeks, in a dose of 30-50 μL per administration.

(29) The eye drop of any of (21) to (25), wherein the concentration of difluprednate is 0.005-0.1% (w/v), and the eye drop is administered for not longer than 12 weeks, 4 times per day for 4 weeks from the start of the administration and twice per day after 4 weeks, in a dose of 30-50 μL per administration.

(30) The eye drop of any of (21) to (25), wherein the concentration of difluprednate is 0.005-0.1% (w/v), and the eye drop is administered for at least 12 weeks, 4 times per day for 4 weeks from the start of the administration and twice per day after 4 weeks, in a dose of 30-50 μL per administration.

(31) Use of difluprednate for the production of an eye drop for treating macular edema.

(32) The use of (31), wherein the macular edema is refractory macular edema.

(33) The use of (31) or (32), wherein the eye drop is an emulsion eye drop.

(34) The use of any of (31) to (33), wherein the concentration of difluprednate in the eye drop is 0.005-0.1% (w/v).

(35) The use of any of (31) to (34), wherein the eye drop comprises 0.005-0.1% (w/v) of difluprednate, and castor oil, polysorbate 80, concentrated glycerin, sodium acetate, boric acid, sodium edetate and sorbic acid.

(36) The use of any of (31) to (35), wherein the concentration of difluprednate in the eye drop is 0.005-0.1% (w/v), the dosing period of the eye drop is at least 1 week, the administration frequency is 4 times per day, and the dose is 30-50 μL per administration.

(37) The use of any of (31) to (35), wherein the concentration of difluprednate in the eye drop is 0.005-0.1% (w/v), the dosing period of the eye drop is 1-4 weeks, the administration frequency is 4 times per day, and the dose is 30-50 μL per administration.

(38) The use of any of (31) to (35), wherein the concentration of difluprednate is 0.005-0.1% (w/v), the administration frequency is 4 times per day for 4 weeks from the start of the administration and twice per day after 4 weeks, and the dose is 30-50 μL per administration.

(39) The use of any of (31) to (35), wherein the concentration of difluprednate is 0.005-0.1% (w/v), the dosing period of the eye drop is not longer than 12 weeks, the administration frequency is 4 times per day for 4 weeks from the start of the administration and twice per day after 4 weeks, and the dose is 30-50 μL per administration.

(40) The use of any of (31) to (35), wherein the concentration of difluprednate is 0.005-0.1% (w/v), the dosing period of the eye drop is at least 12 weeks, the administration frequency is 4 times per day for 4 weeks from the start of the administration and twice per day after 4 weeks, and the dose is 30-50 μL per administration.

Effect of the Invention

According to the present invention, macular edema can be treated with an eye drop. Particularly, the eye drop of the present invention is useful for treating refractory macular edema.

EMBODIMENT OF THE INVENTION

The present invention relates to an eye drop for treating macular edema, which contains difluprednate as an active ingredient.

Difluprednate (6α,9α-difluoroprednisolone 17-butyrate 21-acetate) is a steroidal anti-inflammatory drug like betamethasone phosphate and triamcinolone, and is known to show a superior anti-inflammatory action by transdermal administration and the like. In addition, an eye drop thereof is used for the prophylaxis or treatment of inflammation after surgery and for the prophylaxis or treatment of ocular pain after surgery.

Macular edema is swelling of retinal macula, and the edema occurs due to a liquid leakage from the retinal blood vessels. Macular edema is observed as increased foveal retinal thickness of macula. While the foveal retinal thickness of healthy human varies depending on the individual differences and age, the average value thereof is reported to be 178 μm (Br J Ophthalmol. 1998 September; 82(9): 1003-6). For the treatment of macular edema, photocoagulation by laser irradiation, vitreous surgery, systemic administration of steroid, intravitreal administration and sub-Tenon administration have conventionally been employed as mentioned above, and a certain level of therapeutic effect is found by these treatment methods in some macular edema. On the other hand, it is known that these conventional treatment methods cannot provide a sufficient effect for some macular edema. In the present invention, refractory macular edema refers to macular edema for which a sufficient effect cannot be afforded by the conventionally-employed treatments (e.g., any one or more of photocoagulation by irradiation, vitreous surgery, systemic administration of steroid, intravitreal administration and sub-Tenon administration).

In the present invention, a sufficient treatment effect means that the foveal retinal thickness decreases by not less than 20%. In addition, improvement of logMAR value by not less than 0.2 unit is also considered a sufficient effect. This is a general diagnostic criterium in ophthalmic treatments (FDA/NEI protocol (NEI/FDA Ophthalmic Clinical Trial Design and Endpoints Meeting, 2006)).

The logMAR (the log of the minimum angle of resolution) value shows the ability of the eye (visual acuity) to distinguish the minimum separable acuity, which can be determined by logarithmically converting the values measured using a decimal visual acuity chart.

The foveal retinal thickness is a value from the internal limiting membrane to the visual cell inner segment-outer segment junction in the fovea, and can be measured by Cirrus OCT (registered trade mark, Carl Zeiss), 3D OCT-1000 (registered trade mark, TOPCON CORPORATION) and the like.

The eye drop containing difluprednate as an active ingredient relating to the present invention may take any form of emulsion or suspension. In view of the tissue transitivity of difluprednate, particularly preferred is an emulsion eye drop in the form of an emulsion. Examples of such emulsion eye drop include Durezol (registered trade mark, Sirion Therapeutics, USA). Durezol is a preparation obtained by emulsifying a mixture of difluprednate and predetermined subcomponents for the purpose of enabling difluprednate, the active ingredient, to appropriately penetrate into the eyeball and act on the affected part.

When the eye drop of the present invention is an emulsion, it can be prepared according to, for example, U.S. Pat. No. 6,114,319 (JP-B-3410364).

When the eye drop of the present invention is a suspension, it can be prepared according to, for example, U.S. Pat. No. 5,556,848 (JP-B-3781792).

The concentration of difluprednate contained in the eye drop of the present invention is preferably 0.005-0.1% (w/v), more preferably 0.025-0.1% (w/v), particularly preferably is 0.05% (w/v).

The eye drop of the present invention can be used after mixing with various known pharmaceutically acceptable substances appropriately selected with the aim of adjusting the tissue transitivity upon instillation and the like.

Examples of the pharmaceutically acceptable components include oils (e.g., castor oil, peanuts oil, cottonseed oil, soybean oil, olive oil, medium-chain triglyceride etc.), solvents (e.g., saline, sterilization purified water etc.), stabilizers (e.g., sodium edetate, citric acid etc.), emulsifiers (e.g., polyvinylpyrrolidone etc.), suspending agents (e.g., hydroxypropylmethylcellulose, methylcellulose, hydroxymethylcellulose etc.), surfactants (e.g., polysorbate 80, polyoxyethylene hydrogenated castor oil etc.), preservatives (e.g., benzalkonium chloride, parabens, chlorobutanol etc.), buffers (e.g., boric acid, borax (sodium borate), sodium acetate, citrate buffer, phosphate buffer etc.), isotonicity agents (e.g., sodium chloride, glycerol, mannitol etc.), pH adjusters (e.g., hydrochloric acid, sodium hydroxide etc.) and the like. These various known substances can be appropriately selected and used according to the object.

Particularly, when the eye drop of the present invention is used as an emulsion, it desirably contains a surfactant as an emulsifier. As the surfactant, a nonionic surfactant and the like can be added. Examples of the nonionic surfactant include polyoxyethylene hydrogenated castor oils or polyoxyethylene sorbitan fatty acid ester, preferably sorbitan polyoxyethylene monooleates, polyoxyethylene sorbitan monolaurates, sorbitan polyoxyethylene monopalmitates, sorbitan polyoxyethylene monostearates and the like. Among these, castor oil and polysorbate 80 are preferably contained. Examples of other components that can be contained include concentrated glycerin, sodium acetate, boric acid, sodium edetate and sorbic acid. Particularly preferred are concentrated glycerin, sodium acetate, boric acid, sodium edetate and sorbic acid, which are preferably contained as necessary.

The eye drop of the present invention can be safely administered to mammals (human, dog, rabbit, bovine, horse, monkey, cat, sheep etc.).

While the dose of the eye drop of the present invention varies depending on the level of condition, age and body weight of patient, and the like, for example, an eye drop containing 0.005-0.1% (w/v) of difluprednate is preferably administered to an adult about 2-4 times per day by instillation of 1-2 drops (preferably 1 drop: about 30-50 μL) per administration.

In addition, while the dosing period of the eye drop of the present invention varies depending on the level of condition and the like, for example, it is at least about 1 week, preferably about 1-4 weeks, more preferably about not less than 4 weeks, more preferably not longer than about 12 weeks. Depending on the level of condition and the like, however, administration exceeding 12 weeks may be performed.

In a preferable administration mode, for example, the dosing period of the eye drop of the present invention with a difluprednate concentration of 0.005-0.1% (w/v) is at least 1 week, the administration frequency is 4 times per day, and the dose is about 30-50 μL per administration.

In another preferable administration mode, for example, the dosing period of the eye drop of the present invention with a difluprednate concentration of 0.005-0.1% (w/v) is 1-4 weeks, the administration frequency is 4 times per day, and the dose is about 30-50 μL per administration.

In a still another preferable administration mode, the administration frequency of the eye drop of the present invention with a difluprednate concentration of 0.005-0.1% (w/v) is 4 times per day for 4 weeks from the start of the administration, twice per day after 4 weeks, and the dose is about 30-50 μL per administration.

In a yet another preferable administration mode, the dosing period of the eye drop of the present invention with a difluprednate concentration of 0.005-0.1% (w/v) is not longer than 12 weeks, the administration frequency is 4 times per day for 4 weeks from the start of the administration, twice per day after 4 weeks, and the dose is about 30-50 μL per administration.

In other preferable administration mode, the dosing period of the eye drop of the present invention with a difluprednate concentration of 0.005-0.1% (w/v) is at least 12 weeks, the administration frequency is 4 times per day for 4 weeks from the start of the administration, twice per day after 4 weeks, and the dose is about 30-50 μL per administration.

EXAMPLES

Example 1

The following results were obtained by the clinical tests (UMIN000001432) approved by the Ethics Committee of the Yamagata University Faculty of Medicine.

For confirmation of the efficacy of the eye drop of the present invention, the eyes of 11 patients with macular edema (16 eyes) were treated by instillation of 0.05% (w/v) difluprednate emulsion eye drop (Durezol). The patient group instilled with Durezol included patients who received treatment by sub-Tenon administration of triamcinolone (n=8), intravitreal administration of triamcinolone (n=4), vitreous surgery (n=10) or intravitreal administration of bevacizumab (n=2) (with therapeutic duplication). In addition, photocoagulation was applied to 12 eyes, and an intraocular lens was implanted in 11 eyes. Thus, the patients subjected to the treatment were those who had underwent conventionally-known treatments of macular edema, and were in various conditions particularly due to vitreous surgery and intraocular lens implant. They were patients diagnosed with refractory macular edema who resist improvement of retinal edema near fovea even by these treatments and still have a greater foveal retinal thickness than healthy human. The clinical test was performed by instillation of Durezol to all patients after lapse of not less than 3 months from the previous treatment. The instillation of Durezol was performed 4 times per day for the first 1 month, twice per day for 2 months thereafter. In addition, the dose per administration was 1 drop (about 30-50 μL). The formulation of Durezol is as follows.

| | |
|---|---|
| difluprednate | 0.05 g |
| castor oil | 5.0 g |
| polysorbate 80 | 4.0 g |
| concentrated glycerin | 2.2 g |
| sodium acetate | 0.05 g |
| boric acid | 0.1 g |
| sodium edetate | 0.02 g |
| sorbic acid | 0.1 g |
| sterile purified water | total amount 100 mL |

As a control group, 17 eyes of 9 patients from among patients with the onset of diabetic macular edema were adopted, who were comparable to the Durezol administration group in the age, sex, duration of diabetes and the level of retinopathy. The control group consists of patients before undergoing treatments of macular edema, such as sub-Tenon administration of steroid, intravitreal administration of steroid, vitreous surgery and the like. This control group was administered with a 0.1% (w/v) ophthalmic solution of betamethasone sodium phosphate (Rinderon A, registered trade mark) 6 times per day for 1 month. The betamethasone phosphate eye drop is a steroid preparation generally used as an anti-inflammatory agent for anterior ocular segment in the same manner as an eye drop containing difluprednate.

The above-mentioned administration conditions of Rinderon A are those for the administration of Rinderon A in a test (steroid responder test) previously confirming the level of intraocular pressure increase caused by sub-Tenon administration or intravitreal administration of steroid such as triamcinolone and the like for the treatment of macular edema. The steroid responder test aims to test the sensitivity of individual patient to steroid by measuring the level of intraocular pressure increase resulting from the action, inside the eyeball, of betamethasone phosphate administered by instillation, and it clarifies whether or not macular edema can be treated by intravitreal administration and the like of steroid.

The patients in the Examples of the present invention and the patients in the control group were subjected to the visual acuity test and measurement of decrease rate of the foveal retina thickness using Cirrus OCT (Carl Zeiss), according to the FDA/NEI protocol (NEI/FDA Ophthalmic Clinical Trial Design and Endpoints Meeting, 2006). For the judgment of effectiveness of the instillation treatment, improvement of not less than 0.2 unit in the logMAR value by instillation was judged to be effective for improvement of visual acuity, or not less than 20% of decrease rate of the foveal retinal thickness was judged to be effective. In addition, the effectiveness rate was calculated as a proportion (%) of the number of cases effective for the improvement of visual acuity and foveal retinal thickness decrease rate to the total number of cases.

Table 1 shows the effects of the Durezol instillation and Rinderon A instillation on the foveal retinal thickness decrease rate in macular edema. The effectiveness rate of the foveal retinal thickness decrease is 37.5% in the Durezol administration group at the time point of 1 month from the start of the administration, which clearly shows that the symptom of macular edema is improved. In contrast, in the Rinderon A administration group (control group) (Rinderon A is used as an anti-inflammatory agent for the anterior ocular segment like Durezol), a decrease in the foveal retinal thickness was found in a small portion of patients; however, the effectiveness rate to the total number of patients was extremely low as compared to the Durezol administration group. Considering that the patients of the Durezol administration group are difficult to treat for edema as compared to the patients of the Rinderon A administration group, it is clear that the eye drop of difluprednate of the present invention shows efficacy not obtainable by a betamethasone phosphate eye drop, which is a similar steroid preparation. In addition, it is clear that the difluprednate eye drop is also effective for refractory macular edema, which is difficult to treat by conventional treatment methods.

Table 2 shows time-course changes in the effect of Durezol instillation on the foveal retinal thickness decrease rate. Continuous instillation of Durezol to macular edema patients provides continuous increase in the effectiveness rate, continuous decrease in the average retina thickness of the patients, and administration for 3 months can afford an extremely high effectiveness rate of 61.5%. While the patients of the Durezol administration group had experience of various conventionally-known treatments before the Durezol instillation treatment, similar effectiveness was achieved by the Durezol administration regardless of the treatment history such as vitreous surgery and the like. This indicates that the instilled difluprednate preparation directly acts on the edema site of the macula part. The effect of the eye drop of the present invention is not limited for refractory macular edema, and a similar edema-improving effect is also expected in general patients with macular edema, whose conditions can be improved more easily.

Table 3 shows the effect of Durezol for improvement of visual acuity in macular edema. Table 4 shows time course changes of the effectiveness rate by the Durezol administration in the improvement of visual acuity. Improvement of visual acuity by the treatment of macular edema requires a comparatively long time after improvement of edema in the macula part, and therefore, it is generally difficult to confirm improvement of visual acuity during a short-term treatment. However, apparent improvement of visual acuity was found in a short time in a part of the Durezol administration group, thus showing the effectiveness of the difluprednate eye drop as a method for treating macular edema. On the other hand, an effectiveness rate relative to the improvement of visual acuity was not confirmed in the control Rinderon A administration group. Rinderon A is a steroid used by instillation as an anti-inflammatory agent for the anterior ocular segment, as well as for a steroid responder test in patients with macular edema, as mentioned above, and the results are consistent with the absence of improvement of visual acuity in the steroid responder test.

TABLE 1

| | effectiveness rate after 1 month from start of administration |
|---|---|
| Rinderon A | 5.9% |
| Durezol | 37.5% |

TABLE 2

| after administration | effectiveness rate | average value (μm) of foveal retinal thickness |
|---|---|---|
| 1 week | 37.5% | 407.69 |
| 1 month | 37.5% | 376.13 |
| 2 months | 53.3% | 327.38 |
| 3 months | 61.5% | 302.23 |

TABLE 3

| | effectiveness rate after 1 month from start of administration |
|---|---|
| Rinderon A | 0.0% |
| Durezol | 31% |

TABLE 4

| after administration | effectiveness rate |
|---|---|
| 1 week | 13% |
| 1 month | 31% |
| 2 months | 13% |
| 3 months | 31% |

INDUSTRIAL APPLICABILITY

An eye drop containing difluprednate of the present invention as an active ingredient has enabled improvement of edema in macular edema patients by instillation, which is an administration method with low tissue invasiveness as compared to conventional methods employed in clinical practice. The effects on foveal retinal thickness and visual acuity are superior to those of a betamethasone phosphate eye drop, for which experimental example of instillation administration has been reported. Moreover, effective results can also be obtained in patients with recurrent refractory macular edema, who received sub-Tenon administration or intravitreal administration of triamcinolone, vitreous surgery or intravitreal administration of bevacizumab in the past.

The present invention is based on JP 2009-165924 (filing date: Jul. 14, 2009) filed in Japan, the contents of which are hereby incorporated by reference.

The invention claimed is:

1. A method of decreasing the foveal retina thickness in a mammal with macular edema comprising instilling an emulsion eye drop containing an effective amount of difluprednate to an eye of the mammal, wherein the concentration of difluprednate in the eye drop is 0.05% (w/v).

2. The method according to claim 1, wherein the macular edema is refractory macular edema.

3. The method of claim 2, wherein refractory macular edema is macular edema for which a sufficient effect is not achieved by one or more of the treatments selected from the group consisting of photocoagulation by irradiation, vitreous surgery, systemic administration of steroid, intravitreal administration of a drug, and sub-Tenon administration of a drug.

4. The method of claim 2, wherein the sufficient effect is a decrease of not less than 20% of the foveal retinal thickness after administration.

5. The method of claim 1, wherein the mammal is a human.

6. The method according to claim 1, wherein the emulsion eye drop further comprises castor oil, polysorbate 80, concentrated glycerin, sodium acetate, boric acid, sodium edetate and sorbic acid.

7. The method according to claim 1, wherein the emulsion eye drop is administered for at least 1 week, 4 times per day, in a dose of 30-50 μL per administration.

8. The method according to claim 1, wherein the emulsion eye drop is administered for 1-4 weeks, 4 times per day, in a dose of 30-50 μL per administration.

9. The method according to claim 1, wherein the emulsion eye drop is administered 4 times per day for 4 weeks from the start of the administration and twice per day after 4weeks, in a dose of 30-50 μL per administration.

10. The method according to claim 1, wherein the emulsion eye drop is administered for not longer than 12 weeks, 4 times per day for 4 weeks from the start of the administration and twice per day after 4weeks, in a dose of 30-50 μL per administration.

11. The method according to claim 1, wherein the emulsion eye drop is administered for at least 12 weeks, 4 times per day for 4 weeks from the start of the administration and twice per day after 4 weeks, in a dose of 30-50 μL per administration.

12. The method according to claim 1, wherein the emulsion eye drop further comprises one or more pharmaceutically acceptable components selected from the group consisting of oils, solvents, stabilizers, emulsifiers, suspending agents, surfactants, preservatives, buffers, isotonicity agents, and pH adjusters.

13. The method according to claim 1, wherein the emulsion eye drop further comprises:
- an oil or oils selected from the group consisting of castor oil, peanuts oil, cottonseed oil, soybean oil, olive oil, and medium-chain triglyceride;
- a solvent or solvents selected from the group consisting of saline and sterilization purified water;
- a stabilizer or stabilizers selected from a group consisting of sodium edetate and citric acid;
- a surfactant or surfactants selected from a group consisting of polysorbate 80 and polyoxyethylene hydrogenated castor oil;
- a buffer or buffers selected from a group consisting of boric acid, borax (sodium borate), sodium acetate, citrate buffer, and phosphate buffer;
- an isotonicity agent or isotonicity agents selected from a group consisting of sodium chloride, glycerol, and mannitol; and
- a pH adjuster or pH adjusters selected from a group consisting of hydrochloric acid and sodium hydroxide.

14. A method of decreasing the foveal retina thickness in a mammal with macular edema comprising instilling an emulsion eye drop containing an effective amount of difluprednate to an eye of the mammal, wherein the concentration of difluprednate in the eye drop is 0.05% (w/v), wherein the emulsion eye drop further comprises castor oil, polysorbate 80, concentrated glycerin, sodium acetate, boric acid, sodium edetate, sorbic acid and sterile purified water.

15. A method of improving the visual acuity in a mammal with macular edema comprising instilling an emulsion eye drop containing an effective amount of difluprednate to an eye of the mammal, wherein the concentration of difluprednate in the eye drop is 0.05% (w/v).

16. The method according to claim 15, wherein the macular edema is refractory macular edema.

17. The method of claim 16, wherein refractory macular edema is macular edema for which a sufficient effect is not achieved by one or more of the treatments selected from the group consisting of photocoagulation by irradiation, vitreous surgery, systemic administration of steroid, intravitreal administration of a drug, and sub-Tenon administration of a drug.

18. The method of claim 17, wherein the sufficient effect is an improvement of a logMAR value that is 0.2 or greater after administration.

19. The method of claim 15, wherein the mammal is a human.

20. The method according to claim 15, wherein the emulsion eye drop further comprises castor oil, polysorbate 80, concentrated glycerin, sodium acetate, boric acid, sodium edetate and sorbic acid.

21. The method according to claim 15, wherein the emulsion eye drop is administered for at least 1 week, 4 times per day, in a dose of 30-50 μL per administration.

22. The method according to claim 15, wherein the emulsion eye drop is administered for 1-4 weeks, 4 times per day, in a dose of 30-50 μL per administration.

23. The method according to claim 15, wherein the emulsion eye drop is administered 4 times per day for 4 weeks from the start of the administration and twice per day after 4 weeks, in a dose of 30-50 μL per administration.

24. The method according to claim 15, wherein the emulsion eye drop is administered for not longer than 12 weeks, 4 times per day for 4 weeks from the start of the administration and twice per day after 4 weeks, in a dose of 30-50 μL per administration.

25. The method according to claim 15, wherein the emulsion eye drop is administered for at least 12 weeks, 4 times per day for 4 weeks from the start of the administration and twice per day after 4 weeks, in a dose of 30-50 μL per administration.

26. The method according to claim 15, wherein the emulsion eye drop further comprises one or more pharmaceutically acceptable components selected from the group consisting of oils, solvents, stabilizers, emulsifiers, suspending agents, surfactants, preservatives, buffers, isotonicity agents, and pH adjusters.

27. The method according to claim 15, wherein the emulsion eye drop further comprises:
- an oil or oils selected from the group consisting of castor oil, peanuts oil, cottonseed oil, soybean oil, olive oil, and medium-chain triglyceride;
- a solvent or solvents selected from the group consisting of saline and sterilization purified water;
- a stabilizer or stabilizers selected from a group consisting of sodium edetate and citric acid;
- a surfactant or surfactants selected from a group consisting of polysorbate 80 and polyoxyethylene hydrogenated castor oil;
- a buffer or buffers selected from a group consisting of boric acid, borax (sodium borate), sodium acetate, citrate buffer, and phosphate buffer;
- an isotonicity agent or isotonicity agents selected from a group consisting of sodium chloride, glycerol, and mannitol; and
- a pH adjuster or pH adjusters selected from a group consisting of hydrochloric acid and sodium hydroxide.

28. A method of improving the visual acuity in a mammal with macular edema comprising instilling an emulsion eye drop containing an effective amount of difluprednate to an eye of the mammal, wherein the concentration of difluprednate in the eye drop is 0.05% (w/v), wherein the emulsion eye drop further comprises castor oil, polysorbate 80, concentrated glycerin, sodium acetate, boric acid, sodium edetate, sorbic acid and sterile purified water.

* * * * *